United States Patent [19]

Gordon et al.

[11] Patent Number: 5,109,397
[45] Date of Patent: Apr. 28, 1992

[54] X-RAY TOMOGRAPHY APPARATUS WITH LATERAL MOVEMENT COMPENSATION

[75] Inventors: Bernard M. Gordon, Magnolia; Daniel Abenaim, Lynnfield; Leopold Neumann, Lexington, all of Mass.

[73] Assignee: Analogic Corporation, Peabody, Mass.

[21] Appl. No.: 643,728

[22] Filed: Jan. 22, 1991

Related U.S. Application Data

[63] Continuation-in-part of Ser. No. 579,109, Sep. 6, 1990, abandoned, which is a continuation of Ser. No. 418,920, Nov. 6, 1989, abandoned, which is a continuation of Ser. No. 185,445, Apr. 22, 1988, abandoned, and a continuation-in-part of Ser. No. 181,193, Apr. 13, 1988, abandoned.

[51] Int. Cl.$^5$ .............................................. A61B 6/04
[52] U.S. Cl. ..................................... 378/205; 378/4; 378/20
[58] Field of Search ......... 378/4, 17, 19, 20, 195–198, 378/205–207

[56] References Cited

U.S. PATENT DOCUMENTS

| | | | |
|---|---|---|---|
| 4,015,129 | 3/1977 | Manring | 378/4 |
| 4,032,789 | 6/1977 | Workman | 378/4 |
| 4,053,780 | 10/1977 | Sparks | 378/205 |
| 4,099,059 | 7/1978 | Distler | 378/17 |
| 4,115,695 | 9/1978 | Kelman | 378/17 |
| 4,211,926 | 7/1980 | Nakaya et al. | 378/205 |
| 4,233,507 | 11/1980 | Volz | 378/207 |
| 4,278,888 | 7/1981 | Wagner | 378/206 |
| 4,620,313 | 10/1986 | Erker | 378/19 |
| 4,716,581 | 12/1987 | Bared | 378/198 |
| 4,928,283 | 5/1990 | Gordon | 378/196 |

Primary Examiner—Janice A. Howell
Assistant Examiner—David P. Porta
Attorney, Agent, or Firm—Schiller & Kusmer

[57] ABSTRACT

An improved X-ray tomography system includes means for providing error information at each incremental angular position of the 360° rotation of each scan, indicative of any mechanical lateral movements of the various tomography components during a scan, and means for compensating the data derived from the analog information signals representative of X-ray flux detected by the detectors during each projection view as a function of the error information during the back projection process so as to provide accurate scan data.

41 Claims, 6 Drawing Sheets

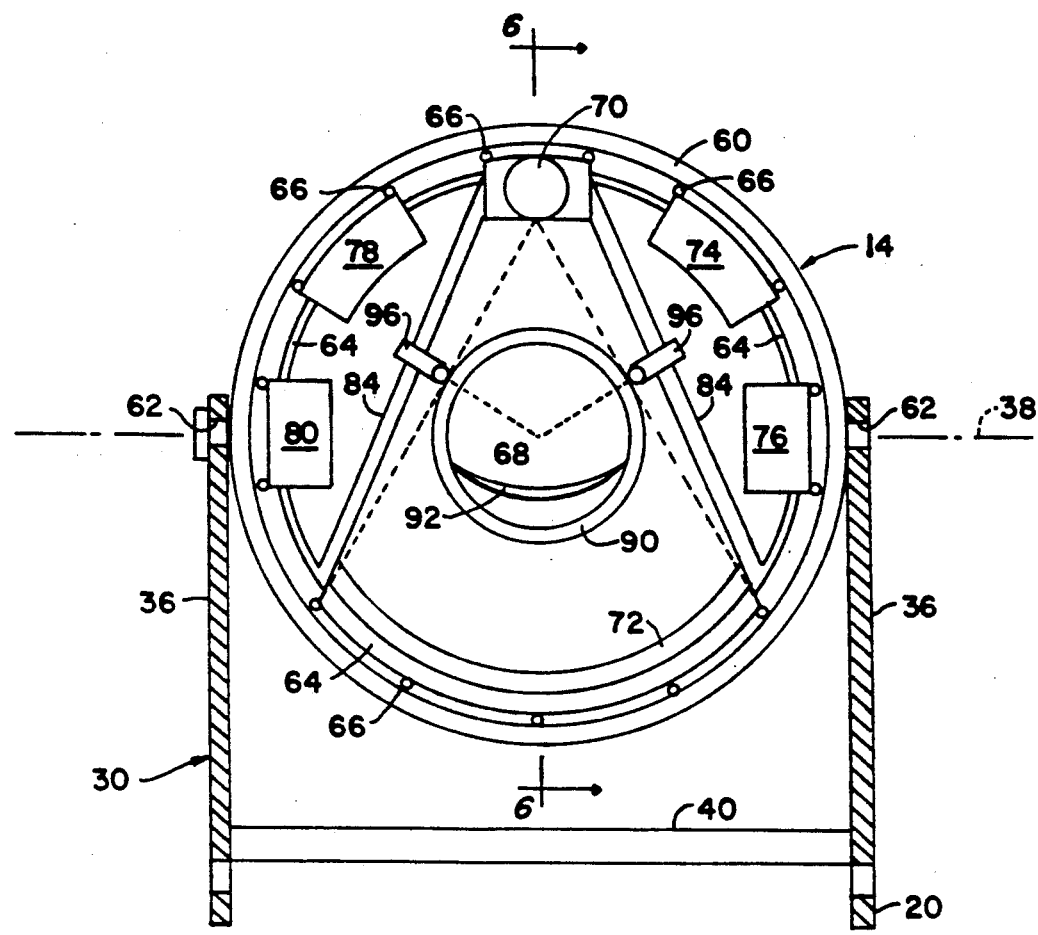
Fig. 2
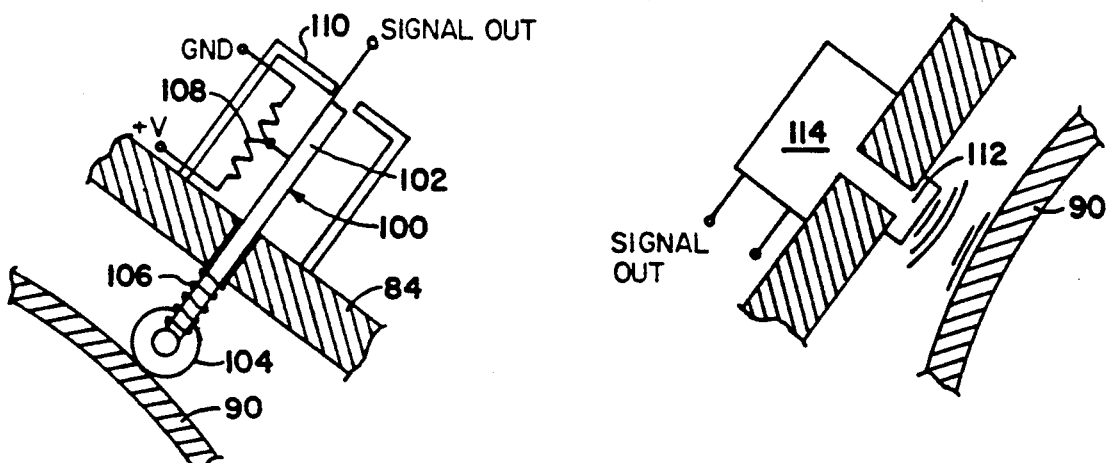
Fig. 3
Fig. 4

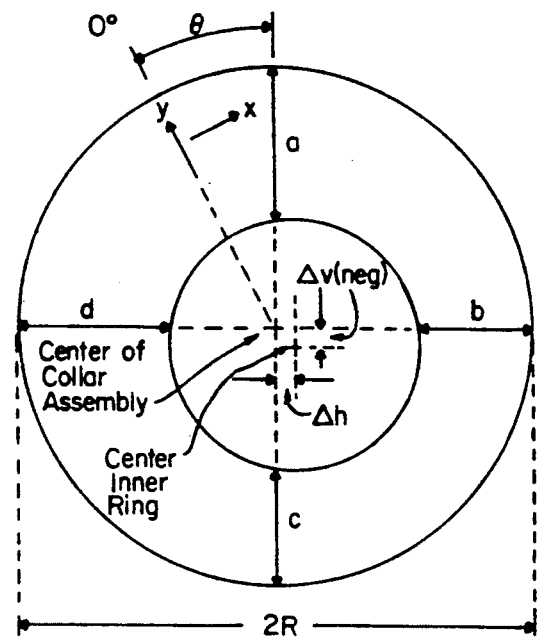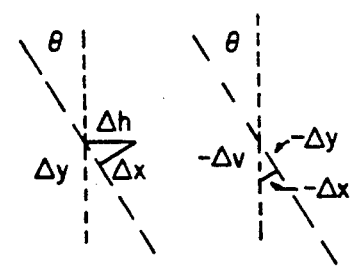
Fig. 9A
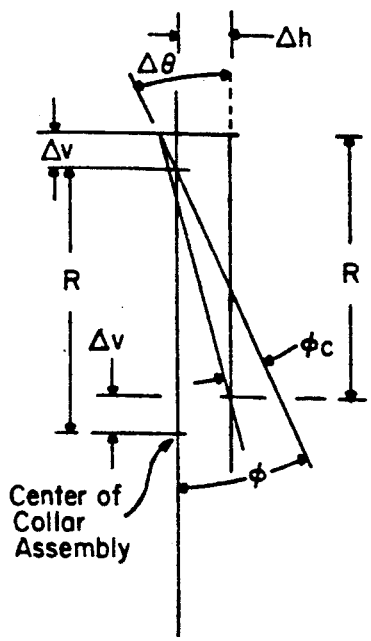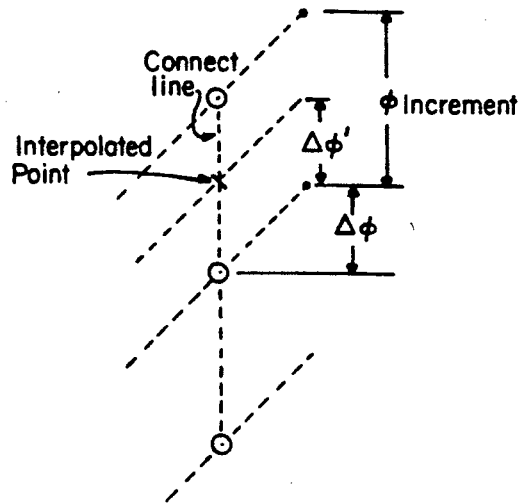
Fig. 9B  Fig. 9C

X-RAY TOMOGRAPHY APPARATUS WITH LATERAL MOVEMENT COMPENSATION

RELATED APPLICATION

The present application is a continuation-in-part application of U.S. patent application Ser. No. 579,109 filed Sep. 6, 1990, now abandoned, which is a continuation application of U.S. patent application Ser. No. 418,920 filed Nov. 6, 1989, now abandoned, which in turn is a continuation application of U.S. patent application Ser. No. 185,445 filed Apr. 22, 1988, now abandoned, the latter being a continuation-in-part application of U.S. patent application Ser. No. 181,193, filed Apr. 13, 1988, now abandoned.

BACKGROUND OF THE INVENTION

The present invention relates generally to tomography systems, and more specifically to the correction of mechanical misalignment errors occurring in one or more projection views of each complete scan of a tomography system.

Tomography systems have been used for many years to create images of cross-sectional slices through objects, and are particularly useful as a diagnostic aid. The most commonly known form is the C.T. (computerized axial tomography) scan system which includes a rotatable gantry supporting an X-ray source and X-ray detectors. The source may provide periodic X-ray pulses, or alternatively, continuous-wave (CW) X-rays. The detectors, usually in the form of gas or solid state detectors for detecting X-ray photons, are disposed on the gantry at predetermined angular spacings relative to the source so as to define a corresponding plurality of X-ray paths from the source to the respective detectors within a common plane of rotation of the gantry. The gantry is normally adapted to rotate through a full 360° rotation so that the source and detectors rotate through a plurality of incremental positions where a corresponding series or set of readings (called "projection views") by the detectors are made. The number of photons absorbed along the various paths through the object, during each sampling period defining each view or set of readings, is a function of the absorption characteristics of the portions of the object along each path during each set of readings. Thus, a plurality of projection views are taken through the portion of an object disposed within the common plane of rotation of the X-ray paths (hereinafter the "plane of rotation"). The detectors generate a corresponding plurality of analog information signals representative of X-ray flux detected by the detectors during each sampling period or projection view.

The output analog information signals of the X-ray detectors acquired from all of the projection views of the 360° rotation, i.e., through all of the incremental angular positions of the 360° rotation within the plane of rotation, are processed, typically through a back projection processing technique, so as to create an image of the two dimensional interior structure of the object exposed to the X-rays.

Great success has been achieved in the development of components, i.e., sources and detectors, for providing data based upon accurately measured X-ray photons during each projection view, as well as improved data acquisition systems for processing the analog information signals provided from the detectors and designed so as to reduce electrical artifact-producing errors, such as gain error, systematically-related radial or displacement-related errors; electrical noise caused by electrical and encoding quantization noise, offset and gain variations, differential non-linearity of encoding devices and dielectric absorption effects, among others.

However, even employing such elaborate electrical compensation schemes errors can still arise due to mechanical misalignments which occur during a scan, or over a number of scans. These errors can be critical when one considers that the above image generation through C.T. scanning by the back projection method is based upon mathematical relationships first developed by Johann Radon. The standard C.T. scan based upon these mathematical relationships assumes that the components of the system, especially the source and detectors, always remain properly mechanically aligned relative to one another during a scan, both throughout each scan and over the course of many scans, and that the components move about an axis of rotation so as to circumscribe a "perfect" circle in the plane of rotation, concentric with the intersection point of the rotation axis with the rotation plane, so as to define a "circular phantom image" of the portion of the object disposed in the circle in the plane of rotation.

The back projection process of reconstructing the phantom image is based on reconstructed values which are derived as a function of the measured data values obtained during each projection view of the scan. Thus, the image data acquired during the scan of the circular phantom image can be used to reconstruct the circular phantom image including the portion of any object in the flux path within the plane of rotation. It should be clear that the X-ray photon measurements themselves must be made extremely accurate relative to each other. Otherwise, the magnitude of systematic or random errors can prevent the determination of the reconstructed values to the degree of accuracy necessary to achieve a reconstructed image to the desired level of quality.

Thus, any mechanical misalignments and lateral movement of the various tomography components during a scan, or those occurring over several scans (which are not correctable using current electronic error correcting techniques) can cause major inaccuracies in reconstructed images. Such images are misleading in their apparent information content and could lead to improper diagnosis by a physician relying on the data. These types of errors can destroy the integrity of the reconstructed image so as to make proper analyses very difficult, if not impossible. In order to help insure that these inaccuracies do not occur, and specifically to minimize vibration and other lateral mechanical movements, which, for example, can occur with wear between parts moving relative to one another, current commercially available C.T. scan systems are typically very large and massive and include a heavy gantry for supporting the source and detectors, with the gantry being rotatably supported in a massive, finely-machined bearing assembly, and an extremely massive and heavy support system for supporting gantry and tomography components.

Such massive systems are extremely expensive to build and once located and constructed for use are extremely difficult to relocate. They require large amounts of floor space and thus cannot be used in space limited environments. Thus, use of such systems, for example, within the operating theatre have been impractical. The result is that a very powerful data gathering diagnostic system is not readily available to a surgeon when such data might be very helpful.

OBJECTS AND SUMMARY OF THE INVENTION

Accordingly, it is a general object of the present invention to provide a tomography system which substantially reduces or overcomes the above-noted problems.

More specifically, it is an object of the present invention to provide a tomography system which compensates for any misalignments of the components of the system so as to provide accurate scan data.

Another object of the present invention is to provide an improved tomography system which provides accurate and consistent scan data throughout each scan rotation and over the course of many scans, regardless of misalignments and lateral movement of the tomography scan components.

And another object of the present invention is to provide an improved tomography system which can be built of less mass and size than comparable systems, and accordingly used in smaller more convenient areas, such as operating theatres, and can be easily moved and relocated as necessary.

Still another object of the present invention is to provide an improved C.T. scan system in which the angle of the plane of rotation can easily be rotated relative to the object being scanned.

These and other objects of the present invention are provided by an improved X-ray tomography system which includes means for providing error information acquired during each scan, and specifically at each incremental angular position of the 360° rotation of each scan where a projection view is taken, indicative of any mechanical misalignments of the various tomography components, and means for compensating the data derived from the analog information representative of X-ray flux detected by the detectors during each sampling period as a function of the error information during the back projection process so as to provide accurate scan data.

In accordance with another aspect of the present invention, means are also provided for easily varying the orientation of the plane of rotation of the tomography components so as to pivot the plane of rotation relative to an object being viewed.

Other objects of the present invention will in part be obvious and will in part appear hereinafter. The invention accordingly comprises the apparatus possessing the construction, combination of elements, and arrangement of parts exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein:

FIG. 2 is a frontal view in cross-section of the gantry of the embodiment shown in FIG. 1;

FIG. 3 is a detailed front view in cross section, partially shown in schematic form, of one embodiment of means for sensing misalignment errors of the tomography components of the FIG. 1 embodiment within the plane of rotation;

FIG. 4 is a detailed front view in cross section of another embodiment of means for sensing misalignment errors of the tomography components of the FIG. 1 embodiment within the plane of rotation;

FIGS. 9A-9C are schematic drawings showing a correction scheme which can be implemented by the FIG. 8 configuration.

DETAILED DESCRIPTION OF THE DRAWINGS

Figure 1:
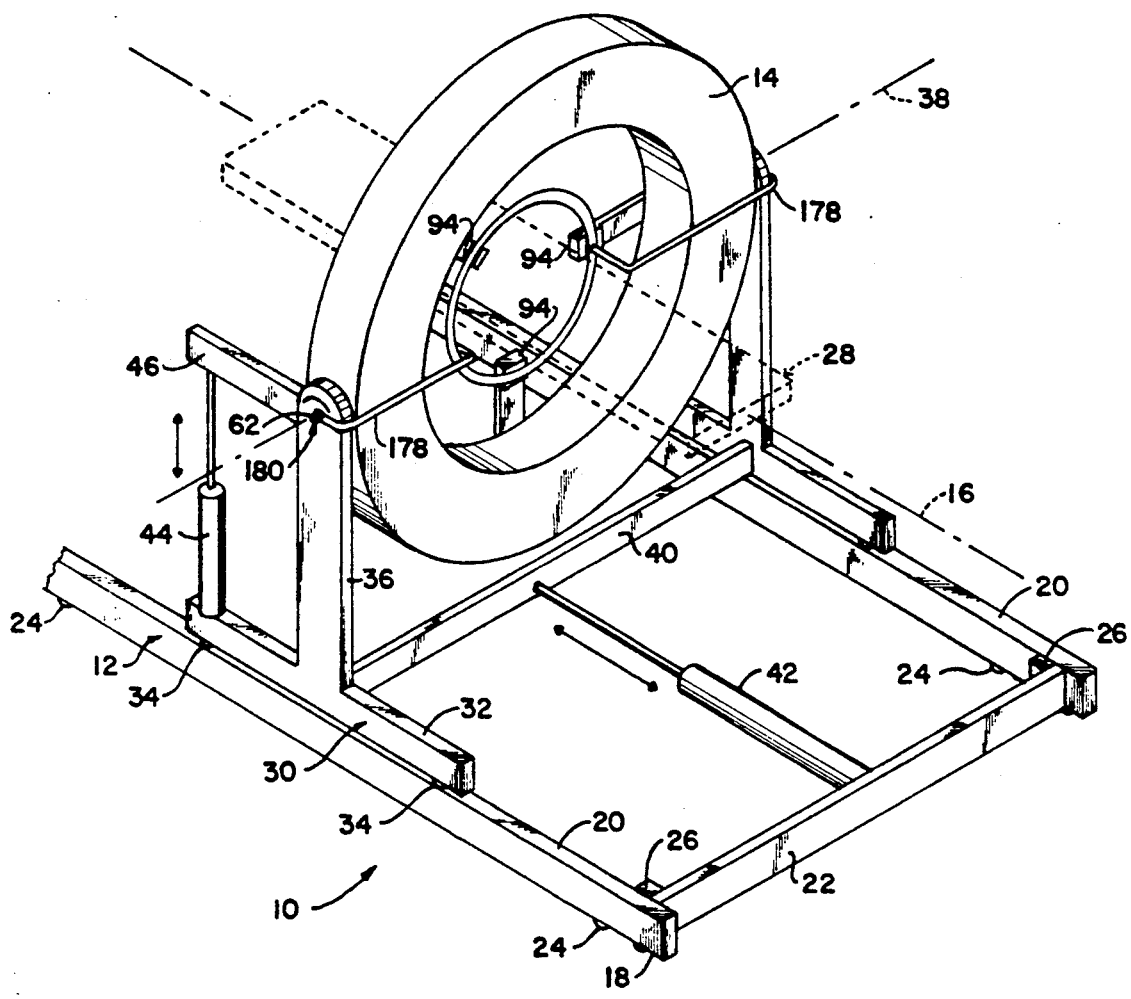
FIG. 1 is a front perspective view of one embodiment of the present invention.

In the drawings the same numerals are used to indicate the same or similar parts, with the same numbers used with small letters indicating similar parts which are modified as described.

Referring to FIG. 1, the preferred tomography system is a C.T. scan system 10 of the fan beam type, although the principles of the present invention can be applied to other types of tomography systems. The system generally includes stationary support assembly 12 for supporting a cylindrical gantry assembly 14. Stationary support assembly 12 is suitably constructed to provide stable support for the gantry assembly so that the tomography components, described hereinafter, can freely rotate about the rotation axis 16, but is constructed to be of relatively small size and mass and easily moveable so that the system can be located at and moved to various locations. As shown for example, the support assembly can be a framed structure made from metal stock, such as stainless steel, so as to provide a base 18 defined by the rails 20 and cross braces 22 (one being shown in FIG. 1). The base 18 can be mounted on wheels 24 so as to easily facilitate movement of the system when necessary, and can include vertically movable jack assemblies 26 so as to lift the system 10 off the wheels 24 once the system is properly located at the site of use.

The stationary support assembly 12 also includes the vertical support frame 28 for supporting the gantry 14, the frame being adapted to be moved along the base 18 so that the gantry can be moved in either direction parallel to rails 20. As shown, the vertical support frame 28 includes side supports 30. Each support 30 has a horizontal bar 32 for receiving wheels 34 for riding on rails 20, and a vertical post 36 preferably for rotatably supporting the gantry 14 about a horizontal axis 38 extending normal to the axis 16. A bottom cross brace 40 connects the bottom of the two side supports. A lever 46 is directly connected to the gantry assembly so that rotation of the lever about the axis 38 rotates the gantry assembly about that axis. Means are provided for selectively moving the vertical support frame 28 along the rails 20 and for selectively rotating the gantry assembly 14 about the axis 16. Preferably, the latter means includes pnuematic or electrical actuators 42 and 44. Actuator 42 is connected between a cross brace 22 and the cross brace 40 so that actuation of the actuator moves the vertical support frame 28 along the rails 20, while actuator 44 is connected between one horizontal bar 32 and lever 46 so that actuation of the latter actuator rotates the gantry about the axis 38.

As best seen in FIG. 2, the gantry assembly 14 is rotatably supported in the side supports 30 at the top of the vertical posts 36. As shown, the assembly 14 includes an outer annular frame 60 having fixed pivot rods 62 extending from diametrically opposite positions of the outer annular frame into suitable bearing assemblies provided in the vertical posts 36 so that the outer annular frame freely rotates about the axis 38. The controls for moving the gantry assembly will be described in greater detail hereinafter.

Continuing with FIG. 2, the gantry assembly 14 also includes an annular collar assembly 64 supported by roller bearings 66 within the outer annular frame 60 so that the collar assembly freely rotates within the frame 60 about the axis 16. The collar assembly has a geometric center 68 and includes the necessary means for supporting the plurality of components for performing C.T. scans. These components include a source 70 of X-ray photons and an array of X-ray detectors 72. The assembly 14 is similar to the assembly shown in U.S. Pat. No. 4,928,283 (issued May 22, 1990 to Bernard M. Gordon for X-Ray Tomography Apparatus, and assigned to the present assignee) in that the assembly also includes a power supply 74 for the source 70, an electronics package 76 for processing analog information signals from the outputs of the detector array 72 and for control of the collar assembly, a power supply 78 for the package 76, and rotational drive means 80, including its own power supply, for causing the collar assembly to rotate within the annular frame 60. The various components are suitably interconnected electrically as is necessary by wires (not shown), which, for example, may be run through hollow electrical conduits secured to the inside of the collar assembly. The patented assembly, however, has been modified to include the present invention.

In addition, in accordance with one aspect of the present invention the assembly includes means for sensing lateral movement of the tomography components in the plane of rotation during each scan. It should be appreciated that the lateral movement can be attributed to a number of sources, such as vibration, and off center rotation of the collar assembly relative to the center 68 due to tolerances and wear in the bearings 66. In the embodiment shown in FIG. 2, a pair of stiffening members 84 are secured to the inside of and as a part of the collar assembly respectively on opposite sides of the source 70 and detectors 72 so as to be symmetrical relative to the source and detector array and the center 68 of the collar assembly. The array of detectors 72 is secured to the inside of an arcuate brace support secured as a part of the collar assembly 64 at equal angular increments about the center 68 so that the array is symmetrically arranged relative to source 70.

In accordance with one embodiment of the present invention the means for sensing the lateral movement of the tomography components includes a non-rotating position reference ring 90. Preferably, as best shown in FIG. 1, the ring is pivotably mounted with pivot pins 62 so that the ring can pivot about the axis 38. Alternatively, the ring can be fixed to the patient table 92 for supporting the patient, as suggested in FIG. 2, or the ring can be secured to the stationary support assembly 12 or side supports 30. The ring is mounted so that it lies within the plane of rotation as the collar assembly rotates during a scan. The diameter of the ring in the plane of rotation should be such that it will lie within the circle circumscribed by the flux, which as described above defines the circular phantom image. Although the ring is preferably positioned so as to be concentric with the collar assembly about the center 68, it should be appreciated that the ring need not be concentric. As will be more apparent hereinafter, the means for sensing the lateral position of the ring within the plane of rotation provides information relating to any nonconcentic positioning of the ring relative to the collar assembly, and the information can be used in the back projection process to ignore any non-concentricities.

The means for sensing the position of the ring within the plane of rotation includes at least two sensors 96 (as seen in FIG. 2) are provided for sensing the relative position of the collar assembly 64 and ring 90 at least at two points within the plane of rotation, with four sensors being necessary in the correction scheme described below in connection with FIG. 9. Preferably, the sensors 96 are secured to the collar assembly 64 (i.e., to the stiffening members 84), and positioned at a 90° increment relative to one another about the center 68 of the collar assembly 64 so that the data detected by the sensors relating to the relative distance between the collar assembly and the ring can be easily translated into X-Y Cartesian coordinate components.

The sensors 96, each may be any type of proximity sensor for detecting relative distance between two elements which move relative to one another in the manner described, such as the electro-mechanical, direct contact type shown in FIG. 3, or the electro-optical, reflected energy, non-contact type shown in FIG. 4. The electro-mechanical type of sensor shown in FIG. 3 includes a cam follower 100, for following the outside surface of the reference ring 90 in the plane of rotation. The follower 100 includes a shaft 102 having a rotatable wheel 104 mounted on its end. The wheel 104 is biased by spring 106 into contact with the outer surface of the ring 90 for rotation in the plane of rotation as the collar assembly rotates about the ring. The shaft 102 supports the tap of a potentiometer 108. The resistor of the latter is fixed within the sensor housing 110 to the respective stiffening member 84. As shown the relative distance between the stiffening member 84 (and thus the collar assembly 64) and the ring 90, at the location of contact of the wheel 104 is a function of the resistance measured between the tap of the potentiometer and system ground. It should be appreciated that a variable capacitor can be used in place of the potentiometer.

The alternative, electro-optical, reflected energy, non-contact type of proximity detector 108 shown in FIG. 4 uses reflected sonic energy to measure the relative distance to the ring 90. A sonic transducer 112 is shown connected to a controller 114. The controller 114 generates signals to the transducer 112 so that the latter transmits short pulses of sound toward the ring 90, and includes a T/R (transmit/receive) switch so that the transducer is also used to receive reflected energy, reflected from the closest point of the outer surface of the collar assembly 90. As is well known, the time delay between the transmission and reception of signals is indicative of the distance between the transducer and the ring. Although the detector is described as a sonic device, it will be appreciated that the device can also use light and radio waves to achieve the same result. Readable coding may also be provided on the ring 90 so as to allow a measurement of angular position to be provided during scanning.

In operation, the sensors 96 function to detect the relative positions between the rotating collar assembly 64 and the stationary reference ring 90 at the locations of the sensors within the plane of rotation 98 as the collar assembly 64 rotates about the rotation axis 16 during a scan. The outputs of the detectors 96 are processed by the electronics package 76 into a digital reading which is used in the backprojection of X-ray data to reconstruct the circular phantom image as described hereinafter. As will be more evident hereinafter, any lateral displacement detected by the sensors 96 due to the non-concentric positioning of the ring 90 relative to the collar assembly 64 will be ignored in the data processing of the analog information signals provided by the array of detectors 72, while any other lateral movement between the collar assembly and the ring, such as movement due to vibration and bearing tolerances or wear, will be taken into account when back projecting the data to produce an image of any object disposed in the circular phantom image area within the plane of rotation as the collar assembly rotates during a scan.

Figure 5:
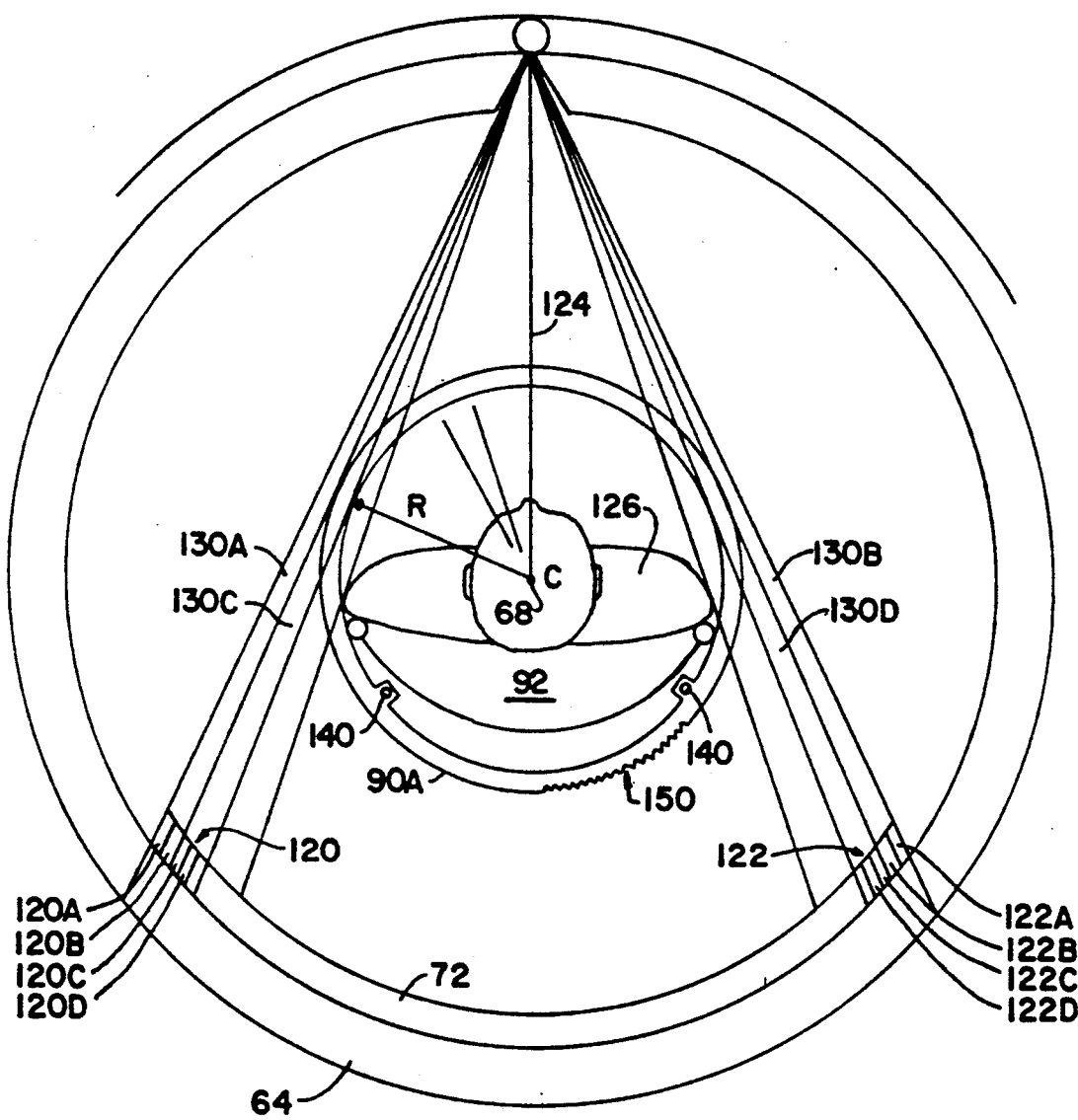
FIG. 5 is a front view taken in cross section illustrating a third embodiment of means for sensing misalignment errors of the tomography components of the FIG. 1 embodiment within the plane of rotation.

FIG. 5 illustrates another embodiment of the means for sensing lateral movement between the rotating collar assembly 64 and stationary reference ring 90a within the plane of rotation of the flux, as the former rotates about the latter. In this embodiment, information relating to any lateral displacement between the collar assembly and the reference ring within the plane of rotation will be provided in the information represented by the X-ray photons traversing the plane of rotation during each projection view of a scan.

More specifically, the ring 90a is modified as described hereinafter. Furthermore, in addition to the array of detectors 72 used to receive X-ray photons from the source 70 during each scan, two sets of additional detectors 120 and 122 are disposed respectively on opposite sides of the array 72, the detectors of each set being spaced at equal angular increments about the center 68. In this embodiment the fan beam is projected at an angle so that flux is projected within the plane of rotation to the array of detectors 72 and also to the detectors 120 and 122, with the ring 90a being sized so that the ring will be disposed in all of the flux paths between source 70 and detectors 72 and between the source 70 and only some of the detectors 120 and only some of the detectors 122. Thus, a sufficient number of detectors 120 and 122 are provided so that the entire ring 90a is disposed in the fan beam of X-rays paths extending from the source 70 to the detectors 72 and at least some of the detectors 120 and some of the detectors 122 during each projection view of a scan. The stationary reference ring 90a is constructed of X-ray translucent material, such as fiber glass, or other composite materials. The X-rays passing through an object placed at or near the center 68 thus also pass through the ring 90a. The X-rays passing through the ring will be attenuated by the ring with the amount of attenuation occurring along the center line 124 of the fan beam (which passes through the center 68) being the smallest (since the X-rays will pass through a minimum amount of material of the ring), and gradually increasing with increasing angle of the X-ray flux path from the center line 124 out towards the edges of the ring (since the X-rays pass through an increasing amount of material). This increasing attenuation of the X-rays with increasing angle from center line 124 is acceptable because the information content received by the detectors 72 about the patient (indicated at 126) is greatest along the center line of the fan beam and decreases as the angle of the flux path from the center line increases. Thus, increased attenuation near the outer edges of the patient is acceptable and even desirable as this decreases the dynamic range of the X-ray signals which must be measured by the detectors 120 and 122.

Thus, as illustrated in FIG. 5, radial vector lines defining the fan beam of X-rays can be drawn from the source 70 and impinge on the detectors 72, as well as some of the detectors 120 and 122. As shown the X-rays radiated along the outer radial lines indicated at 130a and 130b will not be attenuated by the ring and thus the X-rays detected by the detectors 120a, 120b, 122a and 122b will receive relatively unattenuated X-rays, with the latter detectors providing relatively large signals. Conversely, the X-ray flux passing along the radial vector lines indicated at 130c and 130d toward the detectors 120c, 120d, 122c and 122d will be greatly attenuated by the edges of the ring 90a so that a relatively weak signal is received by those detectors, with the weakest signal received by the detectors 120d and 122d where greatest attenuation by the ring has occurred.

In operation the signal outputs of the detectors 120 and 122 can be used to sense lateral shifts between the ring 90a and the collar assembly 64 during each scan. A perceived lateral shift of the source 70 toward the ring 90a will cause the ring to intersect a greater number of radial line vectors so that the detected location of the greatest attenuation will be shifted farther from the center line 124 on each side of the center line. Conversely, a perceived lateral shift of the source 70 away from the ring 90a will cause the ring to intersect a fewer number of radial line vectors so that the detected location of the greatest attenuation will be shifted toward the center line 124 on each side of the center line. Perceived lateral shifts of the source to the right or left (as shown in FIG. 5) of the center line 124 for any particular projection view will result in the detected location of the greatest attenuation for both sides of the center line being shifted in a similar direction. Thus, the outputs cf detectors 120 and 122 can be used to sense lateral shifts of the relative positions of the collar assembly and ring 90. The resolution of the error detection by the structure shown in FIG. 5 is limited by the angular imcrements of X-ray flux through which each of the detectors detect. This resolution can be improved by interpolation technique during the processing of the error correction signals (described hereinafter in connection with FIG. 8) in a manner well known in the art.

In accordance with another aspect of the present invention, the system also includes means for providing during each scan information representative of the quality of the data collected during the scan and used to back project the image of the circular phantom image. The means can include one or more targets, for example two being shown at 140 in FIG. 5, disposed within the plane of rotation within the area of the phantom image (defined by the radius R in FIG. 5) and stationary relative to the ring 90a. The targets may be of a predetermined shape (such as circular as shown), and/or of a predetermined X-ray density different from the ring 90a. Whereas, prior art C.T. scanners typically provide blank images of surrounding structure in the back projection processes, images of any portion of the ring 90a and targets 140 within the circular phantom image can be back projected to provide an image of scan quality as part of and within the back projected image. If just the shape of each of the targets 140 is used, the sharpness of that shape will indicate the sharpness (i.e., resolution) of the entire back projected image and therefore the accuracy of the scan data collected. In this case it would only be necessary for the targets 140 to have a different though not necessarily known X-ray density from that of the ring 90a so that the two can be distinguished from one another. In the event that the X-ray densities of the targets 140 and ring 90a are different and known and thus provide a known measurable difference in contrast (based on density differences) in the back projected image, such a contrast difference based upon a known density difference can be used as a measure of the contrast differences (and therefore densities) between different parts of the body, such as soft tissue and bone, that appear in the back projected image.

Means may also be provided for measuring the angular positions of the source 70 and detectors 72 about the center 68 at each projection view as the latter rotates about the center 68 relative to the patient 126. (As is well known, the patient is preferably positioned at or near the center 68 as shown in FIG. 5, although this is not essential for performing a C.T. scan; an image will be formed so long as the patient is positioned within the circle prescribing the circular phantom image defined by the radius R.) The means is preferably in the form of a detectable pattern predisposed within the plane of rotation stationary relative to the ring 90a. Preferably, the pattern is formed in the ring 90, and as shown can be in the from of slots 150 angularly spaced around a portion of the outer perimeter of the ring. The positions of the slots relative to the source and detectors will differ for each projection view so as to provide data to detectors 72 and/or 120 and/or 122 for each projection view as to the relative angular positions of the source 70 and detectors 72 about the center 68 relative to the patient 126.

In operation of the FIG. 5 embodiment, as with the systems described above, when back projecting an image from data acquired from detectors 72 during a scan, the data acquired from the sensors 94 and the two sets of detectors 120 and 122 can be utilized to sense lateral displacement of the collar assembly 64 relative to the stationary ring 90 while disregarding any non-concentricities between the two.

Figure 6:
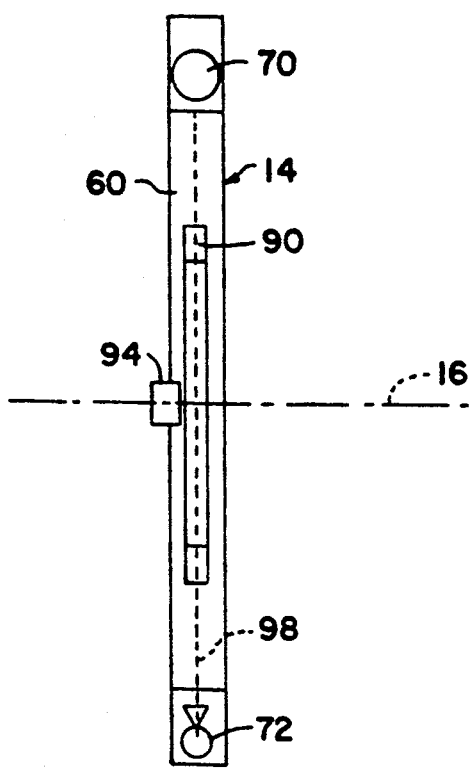
FIG. 6 is a side cross-sectional view taken along line 6—6 in FIG. 2 simplified to show means for sensing misalignment errors of the tomography components normal to the plane of rotation.

In some instances, as for example when performing a helical scan with a helical scan machine, it may be desirable to detect any misalignments or movement normal to the plane of rotation. Accordingly, the means for sensing the position of the reference ring 90 relative to the collar assembly 64 includes means for sensing both the relative position within the plane of rotation and normal to the plane of rotation. The means for sensing relative movement normal to the plane of rotation preferably includes at least one sensor 94 (which can be of the same or similar type as sensor 96) secured to and adapted to rotate with the collar assembly 64 as generally shown in FIGS. 1 and 6. Where it is desirable that the out-of-plane sensors detect any tilt of the ring relative to the plane of rotation, at least three sensors should be used. In the latter case the sensors 94 are preferably equiangularly spaced around the collar and positioned on suitable supports adapted to sense the relative position between the reference ring and each sensor in a direction normal to the plane of rotation (indicated at 98 in FIG. 6) at each sensor location. These sensors will provide three signals representative of any lateral movement of the rotation plane relative to the collar assembly. As will be more evident hereinafter, while the general plane of the ring 90 is co-planar with the plane of rotation 98, and thus parallel to the plane of rotation of the sensors 94, any errors sensed by sensors 94 due to the non-parallelism between the ring and the plane of rotation of the sensors 94 can be compensated for as described in connection with FIG. 8 hereinafter.

Figure 8:
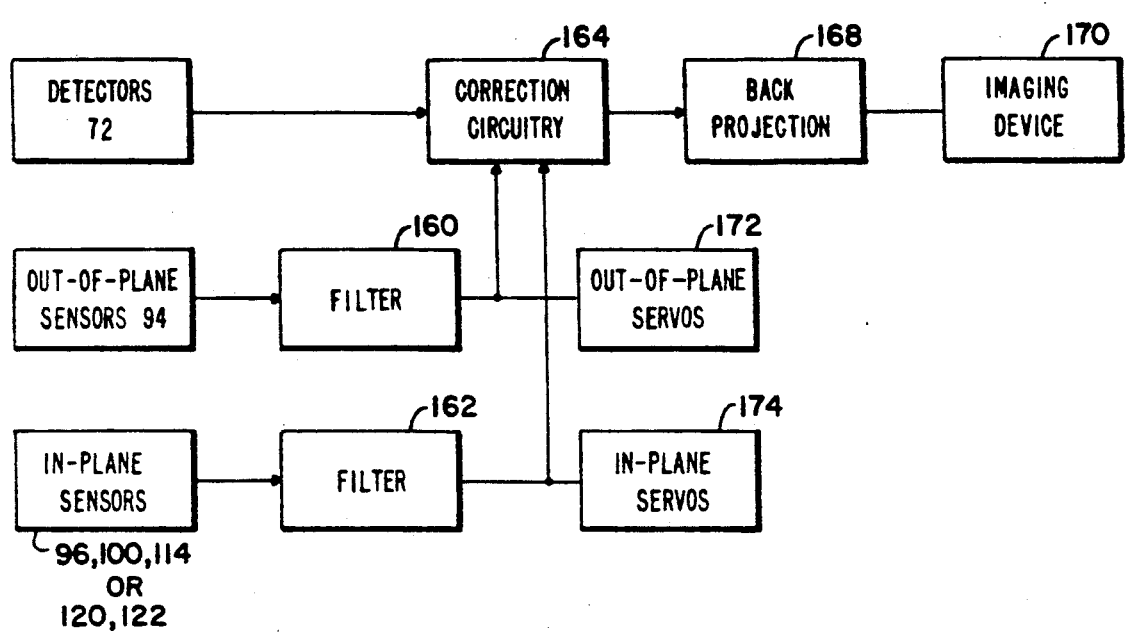
FIG. 8 is a block diagram of the means for providing error correction in the back projection process.

As shown in FIG. 8, the data collected by the out-of-plane sensors 94 (FIGS. 1 and 6) and the in-plane sensors 96 (FIG. 2), 100 (FIG. 3), 114 (FIG. 4), or 120, 122 (FIG. 5) are used to correct the scan data collected by the array of detectors 72. The out-of-plane sensors provide analog information output signals representative of the relative distance between each sensor and the reference ring during each projection view. The output signals of the sensors 94 may be sinusoidally varying as a result of the ring 90 (or 90a) not being precisely disposed in a parallel plane to the plane of rotation of sensors 94. The frequency of the sinusoidally varying component will be equal to the rotational frequency of the gantry during the scan about the axis 16. In such an event the output of the sensors 94 can be demodulated by a filter 160 so that any errors due to the non-parallelism of the ring and the plane of rotation of the sensors 94 will be ignored.

Similarly, the in-plane sensors 96, 100, 114, or 120, 122 provide analog information output signals representative of the relative position between the collar assembly 64 and the reference ring 90 or 90a. Again the output signals of the in-plane sensors may be sinusoidally varying as a result of any non-concentricities between the collar assembly and ring about the center 68. The frequency of the sinusoidally varying component also will be equal to the rotational frequency of the gantry during the scan about the axis 16. In such an event, the output of the in-plane sensors can be demodulated or filtered by a filter 162 so that any errors due to the non-concentricities between the ring and collar assembly also will be ignored.

The signal outputs of filters 160 and 162 can then be applied to position correction circuitry 164 for correcting the data outputs of detectors 72 before those data signals are applied to the back projection system 168. It will be evident that the error information can be applied to servo controls 172 and 174, suitably mounted, for example, on the collar assembly 64 and interactive with the ring 90 so as to provide substantially instantaneous correction at least for gross errors. In this way the correction circuitry 164 need only correct for small errors.

One approach for correcting the data for in-plane errors is illustrated in FIGS. 9A-9C. The correction scheme illustrated relies on four distance measuring sensors, fixedly mounted relative to and adapted to rotate with the collar assembly 64. The sensors are mounted 90° apart as is apparent from FIG. 9A for detecting the distances a, b, c and d, and more particularly the values of $\Delta v$ and $\Delta h$ (the error values representative of the displacement of the center of the ring 90 with the center of the circular phantom image) for each projection view (with the angle $\theta$ representing the relative orientation of the source 70 and detector array 72 so as to define a specific angle for each projection view, and the angle $\theta$ representing the angle of the ray path relative to the center line 124). It can be demonstrated that:

$$\Delta h = (d-b)/2, \quad (1), \text{ and}$$

$$\Delta v = (c-a)/2 \quad (2).$$

In order to recenter for each value of $$\Delta x_\theta = \Delta h_\theta \cos\theta + \Delta v_\theta \sin\theta \quad (3), \text{ and}$$

$$\Delta y_\theta = \Delta h_\theta \sin\theta + \Delta v_\theta \cos\theta \quad (4).$$

Based on the values accumulated over a 360° scan optimum values of a new center defined by $x_c$, $y_c$ are defined by:

$$nx_c = \sum_{0}^{in=360°} \Delta x_\theta; \text{ and} \quad (5)$$

$$ny_c = \sum_{0}^{in=360°} \Delta y_\theta. \quad (6)$$

Once $x_c$ and $y_c$ have been determined then for each value of $\theta$, the new center for each set of data for each projection view can be calculated using the new center to modify $\Delta h$, $\Delta v$ to $\Delta h'$, $\Delta v'$, in accordance with the following relationships:

$$\Delta h'_\theta = \Delta h_\theta - x_c \cos\theta - y_c \sin\theta \quad (7), \text{ and}$$

$$\Delta v'_\theta = \Delta v_\theta - x_c \sin\theta - y_c \cos\theta \quad (8).$$

As shown in FIG. 9B, data is also provided relating to any errors in the actual value of $\theta$ due to lateral misalignments. For small errors in $\theta$, indicated as $\Delta\theta$, the latter can be approximated as:

$$\Delta\theta = \tan^{-1}(\Delta h + \Delta v \cdot \tan\phi)/R \quad (9)$$

Calculating for the optimum angle $\phi_c$ $$\phi_c + \Delta\phi = \phi \quad (10)$$

$$\phi_c - \phi = -\Delta\phi = -\Delta\theta, \text{ where } \Delta\theta = \Delta\phi \quad (11)$$

Thus, data collected for $\theta$, $\phi$ is actually data for $\theta - \Delta\theta$, $\phi - \Delta\phi$.

Where it is desirable to interpolate in $\phi$ based upon the data gathered by the in-plane sensors, FIG. 9C shows a portion of a plot of the possible values of $\theta$ in the vertical direction and the possible values of $\phi$ in the horizontal direction. As shown $$\Delta\phi_c' = \Delta\phi_c(1 + \text{slope of connect line}) \quad (12);$$

Noting that $d(\tan\phi)/d\phi = 1/\cos^2\phi$;

$$\Delta\phi_c' = \Delta\phi_c(1 + (\Delta v/R)(1/\cos^2\phi)) \quad (13).$$

Thus, using the above relationships the data can be corrected by the correction circuitry 164. Using this approach the entire scan must be completed before data correction can be achieved. Accordingly, the circuitry 164 would include sufficient data storage for storing all of the data acquired during a scan.

The back projection system 168 is standard, and may be, for example, the system described in U.S. Pat. No. 4,135,247 issued to Bernard M. Gordon, Leopold Neumann and John Dobbs on Jan. 16, 1979. The back projected image is imaged by an imaging device 170 (e.g., a photographic or xerographic imaging device, or a cathode ray tube) as is well known.

The particular angular position of the collar assembly 64 for each projection view can be determined by synchronizing the time when each of the readings by the detectors 72 are made for each projection view with a reading of the detectors 96, 100, 114, or 120, 122. Alternatively, the angular position of the collar assembly 64 during each projection view can be determined by the position of the pattern of slots 150. The latter technique requires the position correction circuitry 164 to look for and recognize the data representing the slots 150 in the ring 90 and to provide an indication of this location, all within the information contained in the analog output signals provided by the detectors 72 (and/or detectors 120 and/or 122 in the case of the FIG. 5 embodiment). As previously described, the ring 90 (or 90a) provides a uniform variation in intensity across the back projected image by virtue of the fact that the greatest amount of information is obtained along the center line 124 of the fan beam. This information about the ring can be subtracted since its presence should always be the same for each projection view. In addition, the slots 150 will provide a sequential pattern, as for example moving from one side of the fan beam to the center line 124 to the other side of the fan beam as the collar assembly 64 rotates about the ring 90, which can be sensed by the position correction circuitry 164 by comparing sequential data from each successive projection view so as to provide the position information about the angular position of the collar assembly 64 relative to the ring 90 (or 90a).

Figure 7:
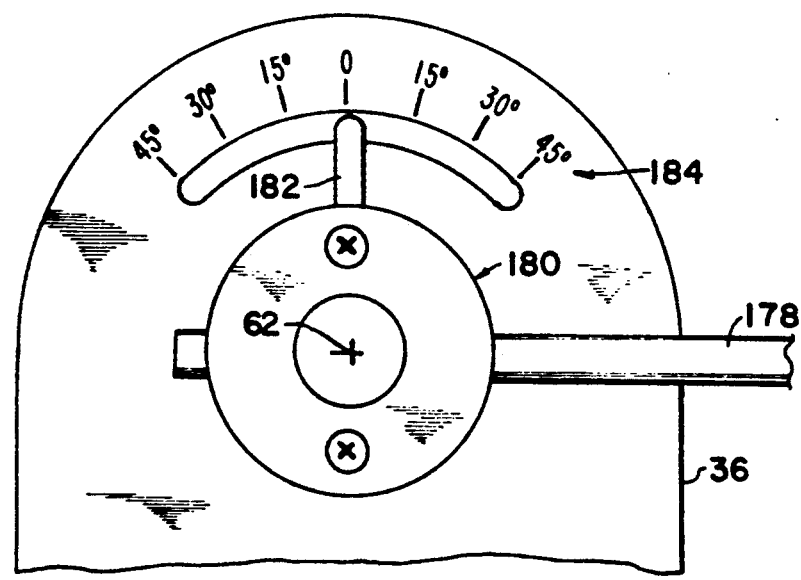
FIG. 7 is a detailed front view of a position sensor for sensing the orientation of the plane of rotation of the tomography components of the FIG. 1 embodiment.
Figure 10:
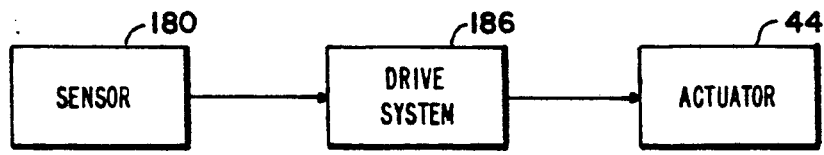
FIG. 10 is a block diagram of the controls for pivoting the gantry so as to pivot the plane of rotation of the tomography elements.

In accordance with another aspect of the present invention, the reference ring 90 or 90a can be mechanically coupled to the collar assembly 64 and both made pivotable about the axis 38 so that the angle of the plane of rotation of the X-ray source and detectors can be easily adjusted relative to the patient 126. More specifically, the reference ring can be separately mounted so that it can be pivoted by the user about the axis 38 as previously described and shown in FIGS. 1 and 2. The ring can be coupled, for example mechanically though coupling links 178 schematically shown in FIG. 1 to an angular position sensor 180 (shown in FIG. 7) designed to mechanically sense the angular position of the plane of the ring. A marker 182, adapted to pivot with the ring about the axis 38, and indicia 184 provided on the vertical side supports 30 can be employed to indicate to the user of the system 10 the angle of the plane of rotation during a particular scan. As shown in FIG. 10, the sensor 180, can be, for example, a shaft encoder or a potentiometer adapted to provide an output signal representative of the angular position of the ring. The output of the sensor 180 is used of operate the drive system 186 for driving the actuator 44 so that the collar assembly moves to the same angular orientation as the ring 90. It should be appreciated that the response time of the drive system 186 and actuator 44 should be fairly fast to insure that the ring 90 will not hit the sensors 94 (if used) when the ring is pivoted about the axis 38.

The foregoing system is an improved tomography scan system which compensates for any mechanical misalignments of the components of the system so as to provide accurate scan data. The improved tomography system provides accurate and consistent scan data throughout each scan rotation and over the course of many scans, regardless of misalignments and lateral movement of the tomography scan components during the scan. Accordingly, the improved tomography scan system can be built of less mass and size than comparable systems, can be used in smaller more convenient areas, such as operating theatres, and can be easily moved and relocated as necessary. Finally, the tomography scan system provides an easy way of adjusting the angle of the plane of rotation of the tomography components relative to the object being scanned.

Since certain changes may be made in the above apparatus without departing from the scope of the invention herein involved, it is intended that all matter contained in the above description or shown in the accompanying drawing shall be interpreted in an illustrative and not in a limiting sense.

What we claim is:

1. In an improved X-ray tomography system of the type comprising: (a) X-ray source means, (b) X-ray detection means, and (c) support means for rotationally supporting said source means and detection means so that (i) said source means and detection means rotate about an axis of rotation through a plurality of angular positions in a scanning plane, (ii) X-rays, emitted by said source means and detected by said detection means, are projected within said scanning plane as the support means rotates about the rotation axis, and (iii) a tomographic image of the portion of an object disposed within said scanning plane can be created from data derived as a function of the X-rays received by the detection means at said plurality of positions, wherein the improvement comprises:

reference means, fixed so that said scanning plane extends through said reference means and said source means and detection means rotate about said reference means through said plurality of positions, for providing error information indicative of any lateral movement of said source means and said detection means relative to said reference means as said support means rotates about said rotation axis; and means for compensating said data as a function of the error information so that said tomographic image is created substantially free of said error information.

2. The apparatus according to claim 1, wherein said means for compensating said data includes means for sensing the relative position between said reference means and said support means, and for generating said error information as a function of said relative position.

3. The apparatus according to claim 2, wherein said means for sensing the relative position between said reference means and said support means includes means for sensing the relative position between said reference means and said support means in at least two directions within said scanning plane.

4. The apparatus according to claim 3, wherein said means for sensing the relative position between said reference means and said support means senses said relative position in two perpendicular directions within said scanning plane.

5. The apparatus according to claim 3, wherein said means for sensing the relative position between said reference means and said support means further includes means for sensing the relative position between said reference means and said support means in a direction normal to said scanning plane.

6. The apparatus according to claim 5, wherein said means for sensing the relative position between said reference means and said support means in a direction normal to said scanning plane includes at least three sensors positioned at three locations for sensing the relative position between said reference means and said support means in a direction normal to said scanning plane at said three locations.

7. The apparatus according to claim 2, wherein said means for sensing the relative position between said reference means and said support means includes proximity detector means for providing a signal representative of the relative distance between the reference means and said support means at the location of said proximity detector means.

8. The apparatus according to claim 7, wherein said proximity detector means includes a non-contacting sensor.

9. The apparatus according to claim 8, wherein said non-contacting sensor includes a source of reflective energy and a detector of said reflective energy.

10. The apparatus according to claim 7, wherein said proximity detector means includes a contacting sensor.

11. The apparatus according to claim 10, wherein said contacting sensor includes a cam follower.

12. The apparatus according to claim 2, wherein a portion of said reference means disposed within said plane is shaped so as to intersect at least some of the X-ray paths between said source means and said detection means at each of said positions, and said means for sensing the relative position between said reference means and said support means includes at least two spaced apart X-ray detectors supported by and secured to rotate with said support means so as to receive X-rays (i) emitted by said source means at each of said positions and (ii) representative of the relative position between said reference means and said support means.

13. The apparatus according to claim 12, wherein said two spaced apart X-ray detectors are positioned on said support means so as to receive X-rays emitted by said source means and passing on opposite sides of said reference means as said support means rotates through said positions.

14. The apparatus according to claim 2, wherein said reference means includes a ring and said plane intersects said ring so as define a circle.

15. The apparatus according to claim 1, wherein said reference means includes a material that is X-ray translucent.

16. The apparatus according to claim 1, wherein said reference means includes means disposed within said plane for indicating the scan quality of said image.

17. The apparatus according to claim 16, wherein said means for indicating the scan quality of said image includes a target disposed within said plane having a predetermined shape.

18. The apparatus according to claim 17, wherein said target is made of a material having a known X-ray density.

19. The apparatus according to claim 1, wherein said reference means defines a reference plane coplanar with said scanning plane when said reference means is properly positioned relative to said support means, wherein said apparatus further includes means for pivotably mounting said reference means relative to said support means so that said reference plane is pivotable relative to said scanning plane about a common pivot axis, and means for moving said support means and said reference means relative to one another about said common pivot axis so that said reference and scanning planes can be properly positioned coplanar with one another.

20. The apparatus according to claim 19, further including means for sensing the angle of said reference means relative to said support means about said pivot axis, and means responsive to said sensed angle for moving said mounting means and reference means relative to one another so as to maintain said reference plane coplanar with said scanning plane.

21. The apparatus according to claim 20, wherein said support means includes a patient table for supporting said subject, and said reference means is a ring affixed to said table.

22. The apparatus according to claim 1, wherein said reference means includes means for defining the angular position of said source means and said detection means relative to said reference means within said scanning plane so that the X-rays received by said detection means include information indicative of each of said plurality of positions.

23. The apparatus according to claim 22, wherein said reference means defines a reference plane, and said apparatus further includes means for sensing the displacement of said reference plane and said scanning plane.

24. In an X-Ray apparatus of the type comprising (1) rotatable means for supporting at least an X-ray source so that said X-ray source rotates about an axis of rotation during X-ray operations, (2) means for sensing X-rays, and (3) means for rotating the rotatable means about the axis of rotation during X-ray operations, wherein the improvement comprises:

means for sensing any lateral displacement of said rotatable means as said rotatable means rotates about the axis of rotation so as to provide position error data during X-ray operations.

25. In an X-ray apparatus of the type comprising (1) rotatable means for supporting at least X-ray source means so that said X-ray source means rotates about an axis of rotation during X-ray operations, (2) means for sensing X-rays, and (3) means for rotating the rotatable means about the axis of rotation during X-ray operations, wherein the improvement comprises:

stationary means positioned relative to said rotatable means so as to remain stationary as said rotatable means rotates about the axis of rotation; and means for determining the relative lateral positional relationship between the rotatable means and the stationary means as said rotatable means rotates about the axis of rotation so as to provide position error data during X-ray operations.

26. The apparatus of claim 25, wherein the rotatable means defines a plane of rotation, and further wherein the relative lateral positional relationship is determined in two orthogonal directions within the plane of rotation.

27. The apparatus of claim 25, wherein the means for determining includes a circularly shaped reference means coaxially located with respect to the axis of rotation and means for detecting the relative lateral position of the guide means with respect to either the rotatable means of the stationary means.

28. The apparatus of claim 27, wherein the reference means is a ring.

29. The apparatus of claim 28, wherein the rotatable means is a rotatable collar which defines a first plane of rotation, and further wherein the ring is positioned during X-ray operations so as to lie within a second plane substantially parallel to or coplanar with the first plane of rotation of the collar.

30. The apparatus of claim 29, wherein the means for detecting includes a pair of position detecting means for detecting the position of the ring within the second plane in two othogonal dimensions.

31. The apparatus of claim 30, wherein the means for detecting includes a third position detecting means for detecting the position of the ring in the dimension substantially perpendicular to the second plane.

32. The apparatus of claim 31, further comprising means for determining positioning of the collar in the dimension substantially perpendicular to the first plane of rotation in response to the third position detecting means.

33. The apparatus of claim 30, wherein the position detecting means include X-ray detectors affixed to the collar and adapted to sense X-rays from the X-ray source means during X-ray operations such that the sensed X-rays contain data which can be used to determine the relative position of the ring and the collar.

34. The apparatus of claim 33, wherein the ring is made of an X-ray translucent material and includes means for enabling observation of scan quality from a resulting image derived from X-ray operations of said apparatus.

35. The apparatus of claim 34, wherein the means for enabling observation of scan quality includes target means having a known shape.

36. The apparatus of claim 34, wherein the means for enabling observation of scan quality includes target means having a known X-ray density.

37. The apparatus of claim 30, wherein the position detecting means include a pair of mechanical position detectors comprising means for providing electrical signals in response to the mechanically detected lateral position of the ring relative to the collar.

38. The apparatus of claim 37, wherein the mechanical position detectors are affixed to the collar and the ring is affixed to the stationary means.

39. The apparatus of claim 30, wherein the means for detecting includes a fourth means for detecting the angular position of the collar with respect to the ring.

40. The apparatus of claim 28, wherein the stationary means includes a patient table means and the ring is affixed to the patient table means.

41. The apparatus of claim 27, wherein the means for detecting includes at least one source of reflective energy and at least one detector for the reflective energy.

* * * * *

UNITED STATES PATENT AND TRADEMARK OFFICE
CERTIFICATE OF CORRECTION

PATENT NO. : 5,109,397
DATED : April 28, 1992
INVENTOR(S) : Bernard M. Gordon, et al.

It is certified that error appears in the above-identified patent and that said Letters Patent is hereby corrected as shown below:

Claim 24, column 15, line 27, delete "X-Ray" and substitute therefor -- X-ray --;

Claim 27, column 16, line 3, delete "of" and substitute therefor -- or --;

Claim 30, column 16, line 15, delete "othogonal" and substitute therefor -- orthogonal --;

Claim 33, column 16, line 26, delete "include" and substitute therefor -- includes --; and Claim 37, column 16, line 44, delete "include" and substitute therefor -- includes --.

Signed and Sealed this

Thirty-first Day of August, 1993

*Attest:*

BRUCE LEHMAN

*Attesting Officer*　　　*Commissioner of Patents and Trademarks*